United States Patent
Antal et al.

(10) Patent No.: US 9,506,103 B2
(45) Date of Patent: Nov. 29, 2016

(54) PROCEDURE FOR BIPHASIC PREPARATION OF LIPOSOMES AND APPLICATION THEREOF IN MANUFACTURING DIAGNOSTIC REAGENTS

(75) Inventors: Jozsef Antal, Budapest (HU); Zoltan Vajda, Budapest (HU); Zsuzsanna Takatsy, Budapest (HU); Beata Nagy, Paszto (HU); Agnes Jakab, legal representative, Budapest (HU); Laslo Jakab, legal representative, Budapest (HU)

(73) Assignee: Diagon Ltd., Budapest (HU)

( * ) Notice: Subject to any disclaimer, the term of this patent is extended or adjusted under 35 U.S.C. 154(b) by 24 days.

(21) Appl. No.: 13/700,627

(22) PCT Filed: May 28, 2010

(86) PCT No.: PCT/HU2010/000063
§ 371 (c)(1),
(2), (4) Date: Mar. 25, 2013

(87) PCT Pub. No.: WO2011/148207
PCT Pub. Date: Dec. 1, 2011

(65) Prior Publication Data
US 2014/0051103 A1    Feb. 20, 2014

(51) Int. Cl.
C12Q 1/56      (2006.01)
A61K 45/00     (2006.01)
A61K 31/683    (2006.01)
C07K 14/745    (2006.01)

(52) U.S. Cl.
CPC .............. *C12Q 1/56* (2013.01); *A61K 31/683* (2013.01); *C07K 14/745* (2013.01)

(58) Field of Classification Search
CPC .................................. C12Q 1/56; A61K 45/00
See application file for complete search history.

(56) References Cited

U.S. PATENT DOCUMENTS

| | | | | |
|---|---|---|---|---|
| 4,522,803 A | * | 6/1985 | Lenk et al. ................... | 424/1.21 |
| 4,849,019 A | * | 7/1989 | Yasukawa ................ | A21D 8/08 |
| | | | | 106/244 |
| 5,160,669 A | * | 11/1992 | Wallach ............... | A61K 9/1272 |
| | | | | 264/4.3 |
| 6,203,816 B1 | * | 3/2001 | Brown .......................... | 424/450 |

* cited by examiner

*Primary Examiner* — Karen Cochrane Carlson
*Assistant Examiner* — Natalie Moss
(74) *Attorney, Agent, or Firm* — Olson & Cepuritis, Ltd.

(57) ABSTRACT

The invention relates to a procedure for biphasic preparation of liposomes, in the course of which technically simple and cheap mechanical mixing methods are used to commingle non-polar organic phase containing an individual mixture of natural and synthetic phospholipids and polar aqueous (buffer) phase not miscible with it, resulting in a liposome emulsion of a unique structure. Furthermore, the invention comprises embodiments of the procedure related to the in vitro diagnostic use of liposomes prepared in this way, when protein type active components are anchored to the surface of liposome membranes without application of any detergents and non-protein type active components are simply mixed with the liposome emulsion of a unique structure. In one of the possible embodiments of the procedure a Prothrombin Time (PT) reagent is prepared. Another possible embodiment of the procedure is the preparation of an activated partial thromboplastin time (APTT) reagent.

5 Claims, No Drawings

PROCEDURE FOR BIPHASIC PREPARATION OF LIPOSOMES AND APPLICATION THEREOF IN MANUFACTURING DIAGNOSTIC REAGENTS

This application is a U.S. National Stage of PCT/HU2010/000063, filed May 28, 2010, which is incorporated herein by reference.

The invention relates to a procedure for biphasic preparation of liposomes, in the course of which non-polar organic phase containing an individual mixture of natural and synthetic phospholipids and polar aqueous (buffer) phase not miscible with it are commingled using a technically simple mechanical procedure. The liposome emulsion of a unique structure prepared by our procedure can be favorably applied in vitro, when an active component is anchored to the surface of liposome membranes.

Moreover, possible embodiments of the invention relate to the preparation of in vitro blood coagulation diagnostic reagents. In a group of embodiments of the invention the referred reagent is composed of our liposome emulsion of a unique structure providing membrane surface for active components and of protein type active components, that is a natural or recombinant tissue factor. In a possible embodiment of this group, the anchoring of protein to the membrane surface is realized on preliminarily prepared liposomes. In a further possible embodiment of this group, the anchoring of protein is carried out simultaneously with the assembly of the liposome membrane surface. In another group of embodiments the referred reagent is composed of our liposome emulsion of a unique structure and of non-protein type soluble active components admixed to the referred emulsion via simple mechanical mixing. Non-protein type soluble active components can be either organic acid(s) or inorganic compound(s) (e.g.: ellagic acid, tannic acid, rutin, quercetin or inorganic silicon dioxide).

The subject of the invention is a procedure, as a possible embodiment of which, in vitro blood coagulation diagnostic reagents are prepared. The in vitro blood coagulation diagnostic reagents prepared by our procedure are suitable for measuring Prothrombin Time and Activated Partial Thromboplastin Time. A further subject of the description is a possible industrial realization of the above-mentioned procedure.

The most commonly performed measurements in blood coagulation diagnostics are aimed at determining the Prothrombin Time (PT) and the Activated Partial Thromboplastin Time (APTT). Both diagnostic procedures monitor the enzymatic processes of the blood coagulation system to indicate the haemostatic status of the examined organism.

Blood coagulation is a cascade-type enzymatic chain reaction consisting of complex amplifying and attenuating biochemical steps. The determinative majority of the enzymatic reactions of the blood coagulation system are membrane-bound processes including protein and non-protein type molecules (enzymes and cofactors) and membrane components. The main constituents of the membrane components are polar and non-polar lipids playing basic structural (anchoring) and functional (e.g. enzyme activity cofactor) roles. For modeling in vivo membrane-bound processes in an in vitro system, membrane functions can be supported by the special procedure of lipidation, furnishing the in vitro system with appropriate lipid components.

According to the invention, the lipid containing components of the in vitro blood coagulation diagnostic reagents are liposomes, that is lipid vesicles with a diameter below the micrometer range, which form stable emulsion with aqueous solutions of appropriate compositions. The referred liposomes provide membrane surface, an environment necessary for in vitro blood coagulation diagnostic reactions, that is they are suitable for anchoring organic compounds (for example natural or recombinant proteins having an appropriate sequence of amino acids) and for associating organic or inorganic compounds bearing appropriate structures. Moreover, surface of liposome membranes serve as cofactor in surface-active reactions of anchored active proteins or of soluble active inorganic compounds.

PT and APTT measurements are aimed at determining the polymerization time of blood plasma fibrinogen as a result of the central step of the blood coagulation system, that is transformation of inactive prothrombin to active thrombin.

PT measurements utilize the coagulation initiating effect of the so-called thromboplastin, that is the initiation of the so-called extrinsic blood coagulation pathway [Madman N. et al. (2007): Arterioscler. Thromb. Vasc. Biol. 27: 1687-1693.]. Thromboplastin comprises tissue factor (TF, coagulation factor III) embedded in phospholipid membrane. Tissue factor is a transmembrane glycoprotein overlapping cell membranes [Bazan J. F.(1990): PNAS 87, 6934-6938.]. Although the detectable level of tissue factor in circulating blood of healthy individuals is disputed [Monroe D. M., Key N. S. (2007): J. Thromb. Haemost. 5: 1097-1105.], upon vascular bed injury, membrane bound tissue factor is released from cells along the injury (e.g. endothelial cells, white blood cells), which initiates the blood coagulation cascade. The released membrane bound tissue factor binds and activates coagulation factor VII, thus membrane bound tissue factor acts as cofactor and receptor of activated coagulation factor VIIa. Membrane bound tissue factor and activated coagulation factor VIIa facilitate the activation of coagulation factor X in the presence of $Ca^{2+}$ ions. The transformation of prothrombin to thrombin is triggered by the prothrombinase complex, which is assembled from activated coagulation factor X (that is factor Xa), and activated coagulation factor V (that is factor Va), the latter serving as a regulating protein. Thrombin cleaves fibrinogen protein chain to result fibrin monomers. Thrombin also activates factor XIII; activated factor XIIIa forms, a ligase enzyme from the transglutaminase family acting as a stabilizing factor of fibrin. The stable fibrin network, the fibrin polymer is created from fibrin monomers by covalent cross-linking under the influence of activated fibrin stabilizing factor XIIIa [Edgington T. S. et al. (1991): The Structural Biology of Expression and Function of Tissue Factor, Thrombosis and Haemostasis, 66: 67-79.].

As described above, thromboplastin is a membrane complex containing tissue factor anchored to a lipid membrane of appropriate composition. Moreover, the presence of the protein combined with a surrounding lipid membrane is pivotal in the initiation of the blood coagulation cascade in space and time. The decisive majority of existing PT reagents is produced through the homogenization of animal or human endothelial tissues rich in lipids with aqueous solutions. However, thromboplastin containing recombinant tissue factor combined with artificial lipid structures is applied in some advanced products.

In APTT measurements the activation cascade is initiated without any tissue factor component (partial thromboplastin), but triggered by active components with a net negative charge (silicon dioxide, organic acids) and lipid membranes.

The known solutions for producing blood coagulation diagnostic reagents are different from each other in respect of the method of preparing the membrane components, that is liposomes. In all methods applied for production of PT reagents, thromboplastin is prepared by mixing a tissue factor kept in solution with the help of a surfactant substance (detergent) and a preformed liposome dispersion [such solutions are described in U.S. Pat. Nos. 5,625,036, 5,314,695, 6,124,110; in U.S. Pat. Nos. 6,733,985, 7,049,087; and in 7,148,067]. Then surfactants are removed from the system by appropriate separation processes that is by dialysis [see for example U.S. Pat. Nos. 5,314,695; 4,622,188; 6,124,110; and U.S. Pat. No. 6,733,985], by ultrafiltration [U.S. Pat. Nos. 5,625,036; and 5,314,695] or by adsorption methods [as described in U.S. Pat. Nos. 7,049,087; and 7,148,067], since the presence of detergents in a proportion higher than 0.05%, inhibit blood coagulation reactions. The process to remove detergent, that is when the concentration of detergent reaches its final value should be inspected by performing several mid-production measurements. A great disadvantage of using detergents, apart from increasing the steps of the procedure, is the high cost of the detergent itself and/or the procedure used for removing it.

In the known procedures the methods for manufacturing liposomes [for example in U.S. Pat. No. 4,622,188] are based on the phenomenon that in solutions of appropriate polarity surface-active substances bearing both polar and non-polar molecule parts form mono- or multi-layer vesicles, depending on the physicochemical conditions.

"A"—The most commonly used classical procedure for manufacturing liposomes is the so-called dry-film method [described in U.S. Pat. Nos. 4,438,052; 5,556,637; and 7,169,410]. In this procedure the first step is dissolving lipids in an organic solvent. Then the solvent is completely evaporated from the solution, with application of vacuum or inert gas flow. The dry lipid film formed on the wall of the vessel finally is dispersed in an appropriate aqueous solution. The final liposome emulsion from this dispersion is produced by intensive mixing [such a solution is described in U.S. Pat. No. 6,296,870] and/or by ultrasound size-reduction [see U.S. Pat. No. 5,234,634]. These known procedures basically resulted in multi-layer liposomes with a rather wide size distribution. Appropriate size distribution and favorable lamination can be accomplished by extrusion of the referred crude dispersion on a high-pressure equipment providing a narrow size distribution and mono or bilamellar vesicles, The extrusion method became widely used in the nineties [examples of this solution are described in U.S. Pat. Nos. 4,529,561; 5,204,112; and 6,926,905].

Depending on water miscibility of the solvent containing lipid, solvent-mixing procedures can be divided into two groups.

In the case of using a solvent miscible with water the procedure is referred to as a monophasic procedure [an example is U.S. Pat. No. 6,261,792].

"B"—In monophasic procedures lipids are dissolved in polar organic solvents, generally in alcohols, and the lipid solution is mixed with an aqueous solvent. The liposomes obtained generally comprise two or more layers, the internal cavity of the liposomes contains aqueous solution and alcohol mixture. In order to reduce the multilamination of the liposomes and narrowing size distribution, methods listed in the case of dry-film technology are used.

"C"—A special case of monophasic procedures is when the lipid mixture is dissolved in aqueous solution using detergent molecules added in relatively high concentration (1-2%). The detergent is removed by ultrafiltration, dialysis or with the help of absorption packing. With this known solution both mono- and multilayer liposomes can be formed, theoretically the proportion of their production can be controlled to a certain extent with the speed of detergent removal and the appropriate ionic composition of the aqueous solution.

In the case of using a solvent not miscible with water the procedure is referred to as a biphasic procedure [see for example U.S. Pat. No. 5,723,147]. In the case of biphasic procedures, further distinction is possible based on the volume ratio of the solvents.

"D"—Traditionally, liposomes produced from lipids dissolved in a small amount of non-polar organic solvent and commingled in a substantially larger amount of aqueous (polar) solvent are referred to as "oil-in-water" emulsions.

"E"—Liposomes produced from lipids dissolved in a large amount of non-polar solvent and commingled with a small amount of water are "water-in-oil emulsions".

In the majority of the known biphasic procedures the phase with a smaller volume is injected into the phase of a larger amount, and an intensive turbulent mixing is used during the entire process. In order to narrow liposome size distribution, these procedures may also be followed by extrusion, or the injection and extrusion are realized in one single step on the same equipment.

Presuming production of monolayer in the case of an "oil-in-water" emulsion the surface of the liposomes are formed by the polar end of the lipid molecules (head), while the non-polar end of the molecules (tail) points towards the non-polar solvent enclosed in the vesicle. In the case of "water-in-oil" emulsions the situation is the opposite. According to theoretical considerations, in the case of complete exclusion of solvents, liposomes are arranged in pseudo-hexagonal lattices, which state is called hexa I ($H_I$) arrangement in the case of "oil-in-water" emulsions and hexa II ($H_{II}$) arrangement in the case of "water-in-oil" emulsions.

It will be appreciated by those skilled in the art that in applications based on anchoring active molecules to a lipid membrane, where the active molecules (e.g. proteins) exert their effects towards the aqueous phase (e.g. diagnostic reagents), the monolayers assembled should be formed exclusively in $H_I$ arrangement. That is, an "oil-in-water" emulsion could be applied as a cellular membrane model. Moreover, in the case of multilayer liposomes, vesicles with such outermost surface layer in which the heads of the lipids point towards the aqueous phase are solely capable of bearing the above mentioned functions.

During critical analysis of the known procedures that can be taken into consideration, we only deal with the ones suitable for producing diagnostic reagents, therefore the methods in group "E" are not subject of comparison.

In general, the methods belonging to groups "A", "B" and "C" result in multilayer liposome emulsions with wide range in size, requiring further physical treatments. The procedures in group "D" mostly result in a narrower size distribution and monolayer liposomes.

A further disadvantage of the dry-film methods included in group "A" is that the preparation of liposomes can be realized with a relatively high number of steps (lipid dissolution, drying, mixing in an aqueous solution, intensive mixing/ultrasound size-reduction). Although these steps can be performed with commercially available and relatively simple devices, actual size distribution can only be controlled with extrusion, which requires expensive equipments. On the market of diagnostic reagents there are no products produced exclusively in this way.

Procedure "B" can be realized in two main steps (lipid dissolution, mixing into an aqueous solution) using the simplest tools, but, similarly to the group "A" methods, further physical processing of the liposomes produced by this way is necessary. That is, the use of an extruder is recommended to adjust the size. The product emulsion and the cavities of the liposomes contain a non-polar organic solvent, the removal of which might be necessary, if required by the application. On the market of diagnostic reagents there are no products produced in this way.

Procedure "C" can also be realized in two steps (dissolving lipid in detergent solution, removal of detergent), but the removal of the detergent is a long and expensive process using any of the known methods (absorption packing material, ultrafiltration or dialysis membrane) and requires expensive and unique equipments (dialyzer, ultrafiltration equipment, filtration equipment/centrifuge, chromatography column and system). The produced liposomes are monolayer or multilayer vesicles, although lamination can be regulated by adjusting the appropriate chemical composition of the solvent. The liposomes of the final product may contain some detergent in their cavities, which might necessitate a further removing step, if required by the application. Application of an extruder is recommended to set the size distribution. On the market of diagnostic reagents there are products produced exclusively in this way [Morrissey and Smith Thromboplastin reagents according to U.S. Pat. No. 7,148,067].

Procedure "D" can be realized in two steps (lipid dissolving, mixing into aqueous solution). However, in order to mix the phases, injectors and mixing equipment designed especially are applied which make the procedure expensive. Liposomes created generally are monolayer vesicles, their size is within a relatively narrow range, but there is organic solvent in the cavities of the liposomes, which might necessitate a further removing step, if required by the application. The use of an extruder is recommended to set the size distribution. On the market of diagnostic reagents there are no products produced in this way.

In method "C", which is well proved and exclusively used for manufacturing liposomes used in diagnostic reagents, the additive (detergent) applied is costly in itself, its removal requires some long and complicated process, which makes the procedure even more expensive. During the process of its removal, the detergent concentration must be inspected by performing several mid-production measurements since any residual detergent may disturb the diagnostic reaction. Although the size distribution of the manufactured product could be controlled to some extent, an extruder (homogenizer) is used for producing the final product, which makes the product even more expensive.

Among the known solutions, no expensive additives are required for methods "A", "B" and "D", but procedures "A" and "B" result in multilayer liposomes with wide size distribution, which make subsequent homogenization unavoidable, consequently they make the manufacturing of the final product expensive.

The aim of the procedure developed by us is to expel disadvantages of the known methods and to elaborate a procedure which technically simplifies the production of liposome emulsions and makes their manufacture cheaper.

Applying method "D" without the expensive injector/mixing equipment, even without any further processing operations, a lipid emulsion of a favorable composition can be obtained. Since the content of liposomes hardly ever gets in the reaction space in diagnostic applications, the organic solvents enclosed in the vesicles do not cause a problem, therefore solvent removal is not necessary. The general arrangement of the invention suits method "D".

The known solutions, according to their physical realization, result in liposomes with wide size distribution and lamination. Liposomes suitable for diagnostic reagents, with 50-100 nm external diameter and assembled with one or two layers of membrane (monolayer and bilayer) are produced by accomplishing subsequent expensive processing steps with high equipment demand (ultrasound size-reduction, filtration, extrusion, centrifugation) and/or requiring surface-active substances. The detergent removal is also necessary in this case, with all the disadvantages accompanying this extra step.

Our procedure is based on the phenomenon that the boundary of phases not miscible with each other serves as a surface for the arrangement of surface-active substances in one single molecule layer (monolayer), like the phospholipid layer in our case. Since our aim is to produce an aqueous emulsion of liposomes, it will be easily appreciated by those skilled in the art that lipids dissolved in a non-polar organic solvent point their polar heads towards the aqueous phase, while their non-polar tail end is directed towards the organic phase. By mixing the phases, the molecule layer, which could be characterized with a zero curvature up to this point, closes up to form a sphere (vesicle). In a large volume of aqueous solution polar heads of the lipids point towards the aqueous phase, and the non-polar tail end of the lipid molecules point towards the non-polar solvent trapped inside the vesicles. In the case of an appropriate proportion of solvents and an appropriate composition and concentration of lipids, entrapment of the whole amount of organic solvents can be attained inside the liposomes. Regarding that when performing diagnostic measurements the content of liposomes hardly ever gets in the reaction space, the organic solvent trapped inside the vesicles does not cause any problem in accomplishing diagnostic measurements, so removal of the solvent is not necessary. If required by the application, the organic solvent trapped in the liposomes can be completely removed through vacuum evaporation or lyophilisation of the liposome emulsion, and the dried emulsion can be dissolved again in an aqueous solution [see the procedure by Janoff et al. according to U.S. Pat. Nos. 4,880,635; 5,578,320; and 5,922,350].

On the basis of our experiences we recognized that the assembly of liposomes takes place by simple mixing (by shaker, vortex mixer, agitator) of phases, that is the smaller volume of non-polar organic phase with an appropriate lipid composition layered under the larger volume of upper polar aqueous (buffer) phase, thus no special injection mixer is needed.

We recognized that in order to produce monolayer liposomes with optimal size distribution, a special mixture of lipid molecules presenting positive or zero curvature is essential. Moreover, by changing the proportion of lipid molecules presenting positive or zero curvature, the diameter of the liposomes can be set optionally within certain limits, thus, ensuring an appropriate lipid composition results in a reproducible way to produce stable emulsions with required size distribution.

We observed that membrane surface of the liposome emulsion of a unique structure created by the above mentioned procedure is suitable for monitoring surface active processes (such as blood coagulation reactions) by having active component(s) anchored to it or simply by cooperating with active molecules in solution.

Our experience showed that anchoring of active molecules to membrane surface of liposome emulsion of a unique structure does not require any additive molecules (e.g. detergent) or physical treatment. Consequently, our liposome emulsion of a unique structure produced by the above mentioned procedure provides appropriate membrane component for in vitro blood coagulation diagnostic reagents, while our procedure can also be extended to other professional fields by involving other optional active components.

We also recognized that tissue factor molecules bearing appropriate non-polar membrane anchor molecule parts integrate in the membrane of our liposome emulsion of a unique structure in the process resulting PT reagent, so the final reagent product can be manufactured during the same process as liposome preparation, in one single step. It will be appreciated by those skilled in the art that the principal condition for single step production is that the active molecule bearing non-polar membrane anchor molecule parts should be contained in the aqueous phase at the beginning of the process when the developing lipid monolayer has a zero curvature. This way the active molecule fitting for the desired orientation (that is pointing towards the membrane with its anchoring end and towards the aqueous phase with its active head) integrates into the developing lipid monolayer on the boundary of phases. If the active molecule were dissolved in the organic phase, during liposome assembly the active head would become located mostly inside the liposome, thus the active component would not be able to exert its effect.

According to our observation, no detergent is necessary to provide the appropriate concentration of tissue factor required for its anchoring to the surface of liposome membranes. As for our experience, the anchoring can be realized by mixing the tissue factor solution of an appropriate composition to preliminarily prepared liposomes, or to the simultaneously assembling liposome membrane surface. Furthermore, we recognized that in diagnostic test systems requiring activated membrane surfaces, the diagnostic reagent can be manufactured simply by mixing an aqueous solution of active components [such as organic acid(s), inorganic compound(s)] with an appropriate composition, to our liposome emulsion of a unique structure.

The invention relates to a biphasic procedure for the preparation of liposomes. The biphasic method described in our invention involves a technically simple and cheap mechanical commingling of non-polar organic phase containing an individual mixture of natural and synthetic phospholipids with polar aqueous (buffer) phase immiscible with the former, thus resulting in a liposome emulsion of a unique structure. Our liposome emulsion of a unique structure providing membrane surface for active components to be anchored to can be favorably entered into applications in vitro, to test surface active reactions.

Among the possible embodiments of the invention, the preparation of in vitro blood coagulation diagnostic reagents is highlighted. In a group of embodiments of the invention the referred reagent is composed of our liposome emulsion of a unique structure and of protein type active components, that is a natural or recombinant tissue factor. The anchoring of protein to the membrane surface is realized on preliminarily prepared liposomes of a unique structure or it is carried out simultaneously with the assembly of the liposome membrane surface. In another group of embodiments of the invention, the referred reagent is composed of our liposome emulsion of a unique structure and of non-protein type soluble active components; their combination is carried out via simple mechanical mixing. The above mentioned non-protein type soluble active components can be for example ellagic acid, tannic acid, rutin, quercetin or inorganic silicon dioxide.

A common feature of in vitro diagnostic reagents prepared by the procedure described in the invention, is the particle (vesicle) size of the stable liposome emulsion of a unique structure, ranging between 50-100 nm. The non-polar organic phase in our procedure is an individual mixture of lipid molecules presenting positive or zero curvature, such as phosphatidylcholine, phosphatidylserine, phosphatidylethanolamine, lysophosphatide acid, lysophosphatidilcholine and a smaller amount of other phospholipids of natural origin, dissolved in the organic phase, with concentration ranging between 0.5-1.5 g/ml and with reaction conditions comprising 55° C. temperature and pH=2.

The above mentioned polar aqueous (buffer) phase in our procedure contains inorganic ions in an appropriately low concentration and pH buffered favorably between 6.0 and 7.4, most favorably pH=6.6 with organic compounds, for example with 0.025 M tricine and supplemented with an antibacterial preservative, for example 0.05 M $NaN_3$. The final pH of the aqueous phase is set by using 5M NaOH solution.

Liposome emulsion of a unique structure is produced by simple mechanical mixing of the two phases described above, in such a way that the non-polar organic phase of a smaller volume is added to the polar aqueous (buffer) phase of a larger volume. The volume ratio of the phases is between 5-50, most favorably is twenty.

Simple mechanical mixing of the polar aqueous (buffer) phase and the non-polar organic phase, the latter layered under the former, can be accomplished by simple shaking together at room temperature (25° C.). It could also be accomplished so that as a result of the rotating motion of agitating element(s) or of the eccentric rotation of the mixing vessel, the phase of a larger volume is brought into vortex motion, then the phase of a smaller volume is injected, sprayed or most favorably dripped into the vortex, at room temperature.

During the biphasic production of the liposome component of our Prothrombin Time (PT) reagent, the non-polar organic phase containing an individual mixture of phospholipids and the polar aqueous (buffer) phase is commingled mechanically as described above, and then, the active component of the PT reagent, the natural or recombinant tissue factor is anchored to the membrane surface of liposomes produced. It can be accomplished for example by mixing the active component (natural or recombinant tissue factor) favorably in a concentration of 0.5-1.0 µM, most favorably 0.8 µM, to the membrane surface of liposomes obtained as a result of simple and cheap mechanical mixing, and then allowing the liposome system containing the anchored tissue factor to rest.

In a different embodiment a tissue factor solution of an appropriate concentration is added to the polar aqueous (buffer) phase applied during liposome assembly, as a result of which protein anchoring is performed simultaneously with the assembly of the liposome membranes.

During the biphasic production of the liposome component of our Activated Partial Thromboplastin Time (APTT) reagent, the non-polar organic phase containing an individual mixture of phospholipids and the polar aqueous (buffer) phase is commingled mechanically as described above. An aqueous solution of the active components of the APTT reagent—organic acid(s), inorganic compound(s)—of an appropriate concentration is admixed to our liposome emulsion of a unique structure as a result of simple and cheap mechanical mixing, and then the liposome system containing the active compound is allowed to rest. In the present procedure the active components can be for example ellagic acid, tannic acid, rutin, quercetin, $SiO_2$ in favorably chosen concentrations (for example ellagic acid: 0.5-1 mM, tannic acid: 1-2%, $SiO_2$: 2-4 g/l).

For the final formulation of the PT and APTT reagents the products produced and allowed to rest as described above, are diluted with buffer solutions of a composition and concentration suiting the respective blood coagulation test, of a favorable pH value, in a proportion of 3:1. In the case of the PT reagent a possible solution for dilution is a buffer solution containing 0.025 M tricine, 0.25 M glycine, 0.11 M NaCl, 0.02 M $CaCl_2$, 0.025 M $NaN_3$, 16 g/l PEG 4000 and 0.0024 M Polybrene, favorably of a pH value between 7.0-7.8, in the present example pH=7.4. In the case of the APTT reagent a possible example is a buffer solution containing 0.25 M glycine, 0.01 M Hepes, 0.001 M $NiSO_4$, 0.2 mM Thimerosal, of a favorable pH value between 6.8-7.8, in the present example pH=7.0.

Both our procedures are characterized by the possibility of further stabilization of the reagents by freeze-drying (lyophilization). Before lyophilization matrix forming additives are used, for example in the following concentrations: mannit 1-3%, sucrose 1-3%, bovine serum albumin 0.1 mM. Lyophilized reagents must be reconstructed with an aqueous solution before use.

The procedure according to the invention is described in detail below.

1. Manufacturing Reagents with Liposomes Prepared in a Preliminary Production Phase Liposome Preparation Composition and Concentration of the Lipid Solution Lipid composition: It will be appreciated by those skilled in the art that the shape and lamination of the liposomes can be influenced by changing the proportion of phospholipids presenting a negative, zero or positive surface curvature according to the shape of their molecules. Obviously the dominance of phospholipids presenting a zero or negative surface curvature support the formation of large flat surfaces, where in an aqueous solution the minimization of surface energy can be realized by folding into layers, therefore phospholipid mixtures of such composition result in large multilayer liposomes or layered laminar lipid aggregates without an enclosed internal space. It is easy to understand that the useful surface of such liposomes, that is, the surface, which enables embedding of active molecules as required (directed towards the aqueous solution), is small as compared to the amount of aggregated lipids. Consequently, phospholipids presenting positive or zero surface curvature are the most suitable for preparing liposomes for the purpose of diagnostic reagents, since they result in liposome vesicles within the desired range of size and shape (spherical). Therefore, the determining proportion of the lipid mixture should be constituted favorably by phosphatidylcholine presenting zero surface curvature and phosphatidylserine presenting a small positive curvature. The size of the liposomes can be favorably influenced by adding a small amount of lyso form molecules, that is molecules containing only one single fatty acid ester with the glycerine skeleton, favorably lysophosphatidylcholine and/or lysophosphatidic acid presenting positive curvature. The high concentration of cholesterol or phosphatidylethanolamine presenting negative surface curvature is to be avoided. Phospholipids isolated from synthetic or natural sources can be used for preparing liposomes. It will be appreciated by those skilled in the art that the phospholipid composition of cellular membrane isolates ensures a desired proportion but the phospholipid composition of sources of vegetable or animal origin varies within a very wide range. While rabbit brain membrane lipid isolates can be used without alteration or additives for preparing recombinant diagnostic reagents, the extract deriving from soy can be used for preparing such liposomes only after adding lysolipids in an appropriate quality and quantity.

Organic solvent composition and concentration: in biphasic procedures a basic requirement relating to organic solvents applied for preparing liposomes is that it must not be miscible with water and it must dissolve the lipids of the desired composition. In practice, mixtures of chloroform and methanol of an appropriate proportion can be used, changing the relative amount of the solvents between the proportions of 5:1 and 1:1, favorably choosing a chloroform-methanol proportion of 2:1. Solubility and characteristics of configuring a certain surface curvature of phospholipids containing a dissociable head group (for example phosphatidylserine) depend significantly on protonation of the head group thus, maintaining the appropriate pH level of the lipid solution during the procedure is of great significance. Favorably the pH value of the lipid solution can be set at the appropriate value with organic acids. Formic acid, acetic acid, trichloroacetic acid or trifluoroacetic acid can be used for this purpose. Application of trifluoroacetic acid is especially favorable due to its volatility. During dissolution of lipids the pH value should be set favorably between 2 and 4, the most suitable value is 2.5. The concentration of trifluoroacetic acid is 0.5%.

Concentration of lipid solutions: since in an aqueous solution phospholipids very easily associate in $H_{II}$ orientation, which is unfavorable from the aspect of the low yield of the active product, it is favorable using high lipid concentrations. Depending on the method of mechanical mixing, lipid concentration can be favorably between 0.2 g/ml and 2 g/ml, the most favorable concentration is 1 g/ml. In this concentration range the chloroform-methanol-phospholipid solution is in a gel state rather than a liquid state.

Temperature of the lipid solution: in order to reach the appropriate lipid concentration temperatures higher than room temperature (25° C.) must be ensured when dissolving lipids. The applicable temperature range is determined by the boiling point of the solvents (chloroform: 61.2° C.; methanol: 64.5° C.) and by the heat stability of the phospholipids. The suitable temperature range is between 30° C. and 55° C., favorably higher temperatures should be used.

Composition and Concentration of the Aqueous Buffer Solution

Composition of the solution: It will be easily appreciated by those skilled in the art that the net charge of the head groups of phospholipids significantly influence their surface curvature characteristics, so ionic composition and ionic strength of the solution determines the quality of the assembling liposomes. Ionic strength, that is roughly the salt concentration of the aqueous phase should be favorably kept at a minimal level, approximately zero. Instead of inorganic salts pH of the solution must be set to the desired value with organic buffers, favorable at a value between pH=6.0 and pH=7.4, most favorably at pH=6.6, adjusted with 5M NaOH solution. Organic substances with a buffer effect suitable for use are favorably MOPS, CHAPS, tricine, glycine. Since liposome emulsions are susceptible to bacterial infections, favorably the solution should contain an antibacterial reagent. Such reagents may be Thimerosal or $NaN_3$, and the concentration of the latter one must be kept at a minimal level due to its $Na^+$ content.

Concentration: the concentration of the buffer component of the aqueous solution used must be sufficient to reach the necessary pH and buffer capacity, that is in the case of tricine the favorable concentration range is between 0.05 and 0.1 M, the optimal concentration is 0.07 M. In the case of using $NaN_3$ as antibacterial reagent the concentration may not be higher than 0.1 M, favorably it should be 0.05 M. A possible aqueous solution composition is shown in the examples described below.

Depending on the mixing method the proportion of the organic and aqueous phase is favorably between 1:5 and 1:100.

Prothrombin Time Reagent Preparation

Aqueous Solution Compositions and Concentrations

Tissue factor (TF) solution: the composition and concentrations of the aqueous buffer solution are the same as the ones determined in the description of the aqueous buffer solution used in liposome preparation. In the case of tricine the favorable concentration range is 0.05-0.1 M, the optimal concentration is 0.07 M and the solution is containing 0.5-1.0 µM, most favorably 0.8 µM of tissue factor. In the case of the antibacterial reagent $NaN_3$, the concentration may not be above 0.1 M, favorably it should be 0.05 M. A possible aqueous solution composition can be seen in the examples below.

Dilution buffer of the liposome emulsion containing active molecules: It will be easily appreciated by those skilled in the art that in the case of blood coagulation reagents the blood coagulation reaction and the quality of the created coagulum, moreover the final quality and shelf-life of the product are highly influenced by the ionic milieu, quantity and quality relations of the additives. This final composition should be favorably adjusted by diluting the solution containing the liposomes and the active molecules. Concentration of $Na^+$ and $Ca^{2+}$ ions, the quality of the counter-ions of the cations, that is the presence of $Cl^-$ and/or $OH^-$ ions have outstanding significance from the aspect of the ionic milieu in this diluting solution. Among the additives influencing the quality of the coagulation reaction and the coagulum, the concentration of $Ni^{2+}$ ions has a significant role, as well as the quality and quantity of the additive polyethylene glycol. From the aspect of the ionic milieu the quality and concentration of the organic buffer components responsible for maintaining the favorable pH range, that is pH=7.0-7.8, is very important. For the reason of maintaining Na concentration at appropriate level final pH value should be favorably set using 5 M NaOH solution. Moreover, quality and quantity of the additive polyethylene glycol also influenced the reagent coagulating abilities. Since the final product contains lipid components susceptible to both oxidation and microbial decomposition, the product should contain antioxidants and antimicrobial agents. Favorably the antimicrobial agent should be $NaN_3$, thus $Na^+$ ion content of which should be taken into consideration when adjusting ionic milieu. If aqueous solution used during liposome preparation did not contain coagulation additive Polybrene, then it should be favorably added to the dilution buffer. A possible solution composition can be seen in the example described below.

Mixing Proportions when Diluting Liposome Emulsion of a Unique Structure Containing Active Molecules Mixing proportions of the diluting solution are determined by the desired characteristics of the final product. Favorably the dilution range should be between 2 and 6 times, 4-times dilution is the most suitable.

Activated Partial Thromboplastin Time Reagent Preparation

Aqueous Solution Compositions and Concentrations

Activating solution: It will be appreciated by those skilled in the art that several different active molecules can be considered (e.g. ellagic acid, tannic acid, rutin, quercetin, $SiO_2$) during the preparation of APTT reagents, and the actual composition and concentration proportion of the solution is determined by their physical and chemical characteristics. In the case of tannic acid the favorably 2% aqueous solution is diluted 1-2 times, most suitable 1.2 times with a solution of a composition and concentration determined as described above in the part of "Composition and concentration of the aqueous buffer solution". A possible aqueous solution composition can be seen in the example below.

Dilution buffer of the liposome emulsion containing active molecules: It will be easily appreciated by those skilled in the art that in the case of blood coagulation reagents the blood coagulation reaction and the quality of the created coagulum, moreover the final quality and shelf-life of the product are highly influenced by the ionic milieu, quantity and quality relations of the additives. This final composition should be favorably reached by diluting the solution containing the liposomes and the active molecules. In the case of the APTT reagent it is important that the dilution solution may not contain $Ca^{2+}$ ions. Concentration of $Na^+$ ions, the quality of the counter-ions of the cations, that is the presence of $Cl^-$ and/or $OH^-$ ions have outstanding significance from the aspect of the ionic milieu in this diluting solution. From the aspect of the ionic milieu the quality and concentration of the organic buffer components responsible for maintaining the favorable pH range, that is pH=6.8-7.8, is very important. For the reason of maintaining Na concentration at appropriate level final pH value should be favorably set using a 5 M NaOH solution. Among the additives influencing the quality of the coagulation reaction and the coagulum, the concentration of $Ni^{2+}$ ions has a significant role. Since the final product contains lipid components that are susceptible to both oxidation and microbial decomposition, the product should also contain antioxidants and antimicrobial agents. Favorably the antimicrobial agent should be Thimerosal. A possible solution composition can be seen in the example described below.

Mixing Proportions when Diluting Liposome Emulsion of a Unique Structure Containing Active Molecules Mixing proportions of diluting solution are determined by the desired characteristics of the final product. Favorably the dilution range should be between 2 and 6 times, 4-times dilution is the most suitable.

2. Preparation of Liposomes and Prothrombin Time Reagent in the Same Procedure

The composition and concentrations of the lipid solution are the same as determined in the description of the lipid composition of the lipid solution used during liposome preparation.

The composition and concentrations of the aqueous buffer solution are the same as determined in the description of the composition of the aqueous buffer solution used during liposome preparation, with the supplementation that in this procedure coagulation additive Polybrene should be favorably added in this solution, favorably in a concentration of 0.024 M.

The proportion of the organic and the aqueous phase is the same as determined in the description of liposome preparation.

The composition and concentrations of the liposome emulsion diluting buffer are the same as determined in the description of the liposome emulsion dilution buffer of the Prothrombin Time reagent.

The mixing proportions of diluting solution of liposome emulsion containing active molecules are the same as determined in the description of the Prothrombin Time reagent.

DETAILED EXAMPLES FOR REALIZATIONS OF THE REAGENTS

1. Liposome Assembly by Layering and Shaking Phases
    a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
    b. At room temperature (25° C.) with the help of a glass syringe 50 μl of the phospholipid solution is carefully layered below 1 ml solution of 0.07 M tricine and 0.05 M $NaN_3$. The pH of the aqueous solution is set to 6.6 using 5M NaOH.
    c. The phases are shaken together at a high speed.
    d. Precipitated lipid granules are removed.
    e. The clear liposome emulsion is mixed with 0.5 ml of 0.8 M recombinant tissue factor dissolved in water. After 10 min rest a 4-times dilution with a solution of 0.025 M tricine, 0.25 M glycine, 0.11 M NaCl, 0.02 M $CaCl_2$, 0.025 M $NaN_3$, 16 g/l PEG 4000 and 0.0024 M Polybrene is applied. The pH of the diluting solution is set to 7.4 using 5M NaOH.
        The quality of the product was checked by performing a Prothrombin Time test.
        The coagulation time measured was 11.9 s on normal control plasma and 17.2 s on pathological control plasma.

2. Liposome Assembly by Dripping Lipid Solution into an Aqueous Phase in Vortex Motion, when the Vortex is Generated with a Magnetic Mixer and Spinning Agitating Element.
    a. 0.5 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
    b. 100 μl of the phospholipid solution is dripped with a syringe into 10 ml solution of 0.07 M tricine and 0.05 M $NaN_3$ brought into rapid vortex motion at room temperature (25° C.). The pH of the aqueous solution is set to 6.6 using 5M NaOH.
    c. Precipitated lipid granules are removed.
    d. The clear liposome emulsion is mixed with 0.5 ml of 0.8 M recombinant tissue factor. After 10 min rest a 4-times dilution with a solution of 0.025 M tricine, 0.25 M glycine, 0.11 M NaCl, 0.02 M $CaCl_2$, 0.025 M $NaN_3$, 16 g/l PEG 4000 and 0.0024 M Polybrene is applied. The pH of the diluting solution is set to 7.4 using 5M NaOH.
        The quality of the product was checked by performing a Prothrombin Time test.
        The coagulation time measured was 11.7 s on normal control plasma and 16.9 s on pathological control plasma.

3. Liposome Assembly by Dripping Lipid Solution into an Aqueous Phase in Vortex Motion, when the Vortex is Generated by the Eccentric Rotation of the Mixing Vessel
    a. 0.5 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
    b. 100 μl of the phospholipid solution is dripped with a syringe into 10 ml solution of 0.07 M tricine and 0.05 M $NaN_3$ brought into rapid vortex motion at room temperature (25° C.). The pH of the aqueous solution is set to 6.6 using 5M NaOH.
    c. Precipitated lipid granules are removed.
    d. The clear liposome emulsion is mixed with 0.5 ml of 0.8 M recombinant tissue factor. After 10 min rest a 4-times dilution with a solution of 0.025 M tricine, 0.25 M glycine, 0.11 M NaCl, 0.02 M $CaCl_2$, 0.025 M $NaN_3$, 16 g/l PEG 4000 and 0.0024 M Polybrene is applied. The pH of the diluting solution is set to 7.4 using 5M NaOH.
        The quality of the product was checked by performing a Prothrombin Time test.
        The coagulation time measured was 11.7 s on normal control plasma and 16.9 s on pathological control plasma.

4. Prothrombin Time Reagent Preparation Using Liposomes Previously Manufactured by Layering and Shaking Phases
    a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
    b. At room temperature (25° C.) with the help of a glass syringe 50 μl of the phospholipid solution is carefully layered below 1 ml solution of 0.07 M tricine and 0.05 M $NaN_3$. The pH of the aqueous solution is set to 6.6 using 5M NaOH.
    c. The phases are shaken together at a high speed.
    d. Precipitated lipid granules are removed.
    e. A 0.8 M aqueous solution of recombinant tissue factor is prepared.
    f. From the liposome emulsion and the solution obtained as described in point e a mixture of a proportion of 2:1 is prepared, and the mixture is allowed to rest for ten minutes.
    g. The liposome emulsion containing incorporated tissue factor is diluted 3 times with a solution containing 0.025 M tricine, 0.25 M glycine, 0.11 M NaCl, 0.02 M $CaCl_2$, 0.025 M $NaN_3$, 16 g/l PEG 4000 and 0.0024 M Polybrene. The pH of the diluting solution is set to 7.4 using 5M NaOH.
        The quality of the product was checked by performing a Prothrombin Time test.
        The coagulation time measured was 11.9 s on normal control plasma and 17.2 s on pathological control plasma.

5. Prothrombin Time Reagent Preparation Using Liposomes Previously Manufactured by Dripping Lipid Solution into an Aqueous Phase in Vortex Motion, when the Vortex is Generated with a Magnetic Mixer and Spinning Agitating Element.
  a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
  b. 100 μl of the phospholipid solution is dripped with a syringe into 10 ml solution of 0.07 M tricine and 0.05 M $NaN_3$ brought into rapid vortex motion at room temperature (25° C.). The pH of the aqueous solution is set to 6.6 using 5M NaOH.
  c. Precipitated lipid granules are removed.
  d. A 0.8 M aqueous solution of recombinant tissue factor is prepared.
  e. From the liposome emulsion and the solution obtained as described in point d a mixture of a proportion of 2:1 is prepared, and the mixture is allowed to rest for ten minutes.
  f. The liposome emulsion containing incorporated tissue factor is diluted 3 times with a solution containing 0.025 M tricine, 0.25 M glycine, 0.11 M NaCl, 0.02 M $CaCl_2$, 0.025 M $NaN_3$, 16 g/l PEG 4000 and 0.0024 M Polybrene. The pH of the diluting solution is set to 7.4 using 5M NaOH.
    The quality of the product was checked by performing a Prothrombin Time test.
    The coagulation time measured was 11.7 s on normal control plasma and 16.9 s on pathological control plasma.

6. Prothrombin Time Reagent Preparation Using Liposomes Previously Manufactured by Dripping Lipid Solution into an Aqueous Phase in Vortex Motion, when the Vortex is Generated by the Eccentric Rotation of the Mixing Vessel
  a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
  b. 100 μl of the phospholipid solution is dripped with a syringe into 10 ml solution of 0.07 M tricine and 0.05 M $NaN_3$ brought into rapid vortex motion at room temperature (25° C.). The pH of the aqueous solution is set to 6.6 using 5M NaOH.
  c. Precipitated lipid granules are removed.
  d. A 0.8 M aqueous solution of recombinant tissue factor is prepared.
  e. From the liposome emulsion and the solution obtained as described in point d a mixture of a proportion of 2:1 is prepared, and the mixture is allowed to rest for ten minutes.
  f. The liposome emulsion containing incorporated tissue factor is diluted 3 times with a solution containing 0.025 M tricine, 0.25 M glycine, 0.11 M NaCl, 0.02 M CaCl2, 0.025 M $NaN_3$, 16 g/l PEG 4000 and 0.0024 M Polybrene. The pH of the diluting solution is set to 7.4 using 5M NaOH.
    The quality of the product was checked by performing a Prothrombin Time test.
    The coagulation time measured was 11.7 s on normal control plasma and 16.9 s on pathological control plasma.

7. Prothrombin Time Reagent Preparation in one Single Step, by in situ Liposome Assembly and Active Component (Tissue Factor) Integration
  a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
  b. A mixture of the solution of 0.07 M tricine and 0.05 M $NaN_3$ with a pH 6.6 adjusted using 5M NaOH and the 0.8 M aqueous solution of recombinant tissue factor of a proportion of 1:1 is prepared.
  c. At room temperature (25° C.) with the help of a glass syringe 50 μl of the phospholipid solution is carefully layered below 1 ml of the solution described in point b.
  d. The phases are shaken together at a high speed.
  e. Precipitated lipid granules are removed.
  f. The liposome emulsion containing the integrated tissue factor is diluted with a solution 3 times its volume containing 0.025 M tricine, 0.25 M glycine, 0.11 M NaCl, 0.02 M $CaCl_2$, 0.025 M $NaN_3$, 16 g/l PEG 4000 and 0.0024 M Polybrene.
    The pH of the diluting solution is set to 7.4 using 5M NaOH.
    The quality of the product was checked by performing a Prothrombin Time test.
    The coagulation time measured was 11.7 s on normal control plasma and 17.0 s on pathological control plasma.

8. Further Stabilization of the Prothrombin Time Reagent Produced by in situ Liposome Assembly and Active Component (Tissue Factor) Integration Through Lyophilisation, when the Matrix-Forming Additive is Bovine Serum Albumin
  a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
  b. A mixture of the solution of 0.07 M tricine and 0.05 M $NaN_3$ with a pH 6.6 adjusted using 5M NaOH and the 0.8 M aqueous solution of recombinant tissue factor of a proportion of 1:1 is prepared.
  c. At room temperature (25° C.) with the help of a glass syringe 50 μl of the phospholipid solution is carefully layered below 1 ml of the solution as described in point b.
  d. The phases ware shaken together at a high speed.
  e. Precipitated lipid granules are removed.
  f. As a matrix forming additive, bovine serum albumin (BSA) is added to the product, favorably in a concentration of 0.1 mM.
  g. The emulsion as obtained to point f is filled into a lyophilization vial.
  h. The content of the vial above is lyophilized.
  i. Before use the lyophilized substance is dissolved in 4 ml solution of 0.025 M tricine, 0.25 M glycine, 0.11 M NaCl, 0.02 M $CaCl_2$, 0.025 M $NaN_3$, 16 g/l PEG 4000 and 0.0024 M Polybrene. The pH of the dissolving solution is set to 7.4 using 5M NaOH.
    The quality of the product was checked by performing a Prothrombin Time test. The coagulation time measured was 12.4 s on normal control plasma and 19.8 s on pathological control plasma.

9. Further Stabilization of the Prothrombin Time Reagent Produced by in situ Liposome Assembly and Active Component (Tissue Factor) Integration Through Lyophilization, when the Matrix-Forming Additive is Mannit
  a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
b. A mixture of the solution of 0.07 M tricine and 0.05 M NaN$_3$ with a pH 6.6 adjusted using 5M NaOH and the 0.8 M aqueous solution of recombinant tissue factor of a proportion of 1:1 is prepared.
c. At room temperature (25° C.) with the help of a glass syringe 50 μl of the phospholipid solution is carefully layered below 1 ml of the solution as described in point b.
d. The phases are shaken together at a high speed.
e. Precipitated lipid granules are removed.
f. As a matrix-forming additive, mannit is added to the product, favorably in a concentration of 1-3%.
g. The emulsion as obtained to f is filled into a lyophilization vial.
h. The content of the vial above is lyophilized.
i. Before use the lyophilised substance is dissolved in 4 ml solution of 0.025 M tricine, 0.25 M glycine, 0.11 M NaCl, 0.02 M CaCl$_2$, 0.025 M NaN$_3$, 16 g/l PEG 4000 and 0.0024 M Polybrene. The pH of the dissolving solution is set to 7.4 using 5M NaOH.
The quality of the product was checked by performing a Prothrombin Time test. The coagulation time measured was 12.7 s on normal control plasma and 17.7 s on pathological control plasma.

10. Further Stabilization of the Prothrombin Time Reagent Produced by in situ Liposome Assembly and Active Component (Tissue Factor) Integration Through Lyophilization, when the Matrix-Forming Additive is Sucrose
a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
b. A mixture of the solution of 0.07 M tricine and 0.05 M NaN$_3$ with a pH 6.6 adjusted using 5M NaOH and the 0.8 M aqueous solution of recombinant tissue factor of a proportion of 1:1 is prepared
c. At room temperature (25° C.) with the help of a glass syringe 50 μl of the phospholipid solution is carefully layered below 1 ml of the solution as described in point b.
d. The phases are shaken together at a high speed.
e. Precipitated lipid granules are removed.
f. As a matrix-forming additive, sucrose is added to the product, favorably in a concentration of 1-3%.
g. The emulsion as obtained to f is filled into a lyophilization vial.
h. The content of the vial above is lyophilized.
i. Before use the lyophilized substance is dissolved in 4 ml solution of 0.025 M tricine, 0.25 M glycine, 0.11 M NaCl, 0.02 M CaCl$_2$, 0.025 M NaN$_3$, 16 g/l PEG 4000 and 0.0024 M Polybrene. The pH of the dissolving solution is set to 7.4 using 5M NaOH.
The quality of the product was checked by performing a Prothrombin Time test. The coagulation time measured was 12.7 s on normal control plasma and 17.7 s on pathological control plasma.

11. Activated Partial Thrombin Time Reagent Preparation Using Liposomes Previously Manufactured by Layering and Shaking Phases
a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
b. A mixture of the solution of 0.07 M tricine and 0.05 M NaN$_3$ with a pH 6.6 adjusted using 5M NaOH and the 0.8 M aqueous solution of recombinant tissue factor of a proportion of 1:1 is prepared
c. At room temperature (25° C.) with the help of a glass syringe 50 μl of the phospholipid solution is carefully layered below 1 ml of the solution as described in point b.
d. The phases are shaken together at a high speed.
e. Precipitated lipid granules are removed.
f. 2% aqueous stock solution of tannic acid is prepared.
g. The 2% stock solution of tannic acid is diluted by 1.2 times with a solution of 0.07 M tricine and 0.05 M NaN$_3$.
h. From the liposome emulsion as obtained to point e and the solution as obtained to g a mixture of a proportion of 1:1 is prepared, and is allowed to rest for ten minutes.
i. The liposome emulsion containing tannic acid is diluted by 3 times with a solution containing 0.07 M mannit, 0.25 M glycine, 0.01 M Hepes, 0.001 M NiSO$_4$, 0.2 mM Thimerosal. The pH of the diluting solution was set to 7.0 using 5M NaOH.
The quality of the product was checked by performing an Activated Partial Thrombin Time test. The coagulation time measured was 40.1 s on normal control plasma and 76.9 s on pathological control plasma.

12. Activated Partial Thrombin Time Reagent Preparation Using Liposomes Previously Manufactured by Dripping Lipid Solution into an Aqueous Phase in Vortex Motion, when the Vortex is Generated with a Magnetic Mixer and Spinning Agitating Element.
a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
b. 100 μl of the phospholipid solution is dripped with a syringe into 10 ml solution of 0.07 M tricine and 0.05 M NaN$_3$ brought into rapid vortex motion at room temperature (25° C.). The pH of the aqueous solution is set to 6.6 using 5M NaOH.
c. Precipitated lipid granules are removed.
d. 2% aqueous stock solution of tannic acid is prepared.
e. The 2% stock solution of tannic acid is diluted by 1.2 times with a solution of 0.07 M tricine and 0.05 M NaN$_3$.
f. From the liposome emulsion and the solution as obtained to point e a mixture of a proportion of 1:1 is prepared, and the mixture is allowed to rest for ten minutes.
g. The liposome emulsion containing tannic acid is diluted by 3 times with a solution containing 0.07 M mannit, 0.25 M glycine, 0.01 M Hepes, 0.001 M NiSO$_4$, 0.2 mM Thimerosal. The pH of the diluting solution was set to 7.0 using 5M NaOH.
The quality of the product was checked by performing an Activated Partial Thrombin Time test. The coagulation time measured was 36.2 s on normal control plasma and 60.5 s on pathological control plasma.

13. Activated Partial Thrombin Time Reagent Preparation Using Liposomes Previously Manufactured by Dripping Lipid Solution into an Aqueous Phase in Vortex Motion, when the Vortex is Generated by the Eccentric Rotation of the Mixing Vessel a. 1 g of phospholipid mixture isolated from rabbit brain powder is dissolved in 1 ml of a chloroform-methanol mixture of a proportion of 2:1 containing 0.5% trifluoroacetic acid. The obtained mixture of gel is kept in liquid state at 55° C.
  b. 100 µl of the phospholipid solution is dripped with a syringe into 10 ml solution of 0.07 M tricine and 0.05 M $NaN_3$ brought into rapid vortex motion at room temperature (25° C.). The pH of the aqueous solution is set to 6.6 using 5M NaOH.
  c. Precipitated lipid granules are removed.
  d. 2% aqueous stock solution of tannic acid is prepared.
  e. The 2% stock solution of tannic acid is diluted by 1.2 times with a solution of 0.07 M tricine and 0.05 M $NaN_3$.
  f. From the liposome emulsion and the solution as obtained to point e a mixture of a proportion of 1:1 is prepared, and the mixture is allowed to rest for ten minutes.
  g. The liposome emulsion containing tannic acid is diluted by 3 times with a solution containing 0.07 M mannit, 0.25 M glycine, 0.01 M Hepes, 0.001 M $NiSO_4$, 0.2 mM Thimerosal. The pH of the diluting solution is set to 7.0 using 5M NaOH.

The quality of the product was checked by performing an Activated Partial Thrombin Time test. The coagulation time measured was 36.2 s on normal control plasma and 60.5 s on pathological control plasma.

The most important technical advantage of the methods described above for manufacturing blood coagulation reagents is that they can be realized using simple and cheap equipments (mixer) and reagents. No detergent is used, therefore there is no need to remove it, and there is no need for any further processing of the produced liposome (such as extrusion).

The most important economic advantage of the invention is that it does not demand expensive reagents and procedures for liposome preparation, it does not require the use of detergents for dissolving the tissue factor, and the obtained liposome is suitable for producing blood coagulation reagents directly, without any subsequent processing. A further economic advantage is that the invention can also be realized in such a way that liposome assembly and reagent production can take place in one single step, as a result of which further costs can be saved. The PT reagent manufactured using the method described in the invention presents biochemical characteristics identical to those of thromboplastin isolated from natural sources.

The invention claimed is:

1. A procedure for biphasic preparation of liposomes having particle size of 50-100 nm, said procedure comprising:
    preparing a non-polar organic phase comprising mixture of chloroform-methanol in a proportion of 2:1 and a mixture of natural and synthetic phospholipids to form a non-polar organic phase;
    adding the non-polar organic phase to a polar aqueous phase not miscible with the non-polar organic phase, said polar aqueous phase is provided with 0.025 M tricine, the pH value of the polar aqueous phase is set between pH=6 and pH=7.4 using NaOH, and is supplemented with antibacterial NaN3 preservative in a concentration of 0.05 M, wherein the volume of the non-polar organic phase is added to a 5 to 50 times larger volume of the polar aqueous phase;
    mechanically commingling both the non-polar organic phase and the polar aqueous phase in a manner sufficient for a monolayer or bilayer liposome membrane to completely enclose the organic phase to produce an oil-in-water liposome emulsion;
    wherein a liposome emulsion prepared in this way is suitable for anchoring an active component to form a diagnostic reagent.

2. The procedure of claim 1, wherein the non-polar organic phase is layered under the polar aqueous phase prior to said mechanical comingling.

3. The procedure as in claim 1, wherein said mechanical comingling comprises vortexing the polar aqueous phase at room temperature and injecting, spraying or dripping the non-polar organic phase into the polar aqueous phase.

4. The procedure as in claim 1 wherein the lipids are selected from the group consisting of phosphatidylcholine, phosphatidylserine, phosphatidylethanolamine, lysophosphatidic acid, and lysophosphatidylcholine.

5. The procedure as in claim 1 wherein the phospholipid concentration is 1 g/ml.

* * * * *